(12) United States Patent
Liu et al.

(10) Patent No.: US 9,498,489 B2
(45) Date of Patent: *Nov. 22, 2016

(54) ANTIMETABOLITE AGENT COMBINATIONS IN THE TREATMENT OF CANCER

(75) Inventors: Lili Liu, Macedonia, OH (US); Stanton Gerson, Hunting Valley, OH (US)

(73) Assignee: Case Western Reserve University, Cleveland, OH (US)

( * ) Notice: Subject to any disclaimer, the term of this patent is extended or adjusted under 35 U.S.C. 154(b) by 1233 days.

This patent is subject to a terminal disclaimer.

(21) Appl. No.: 12/762,768

(22) Filed: Apr. 19, 2010

(65) Prior Publication Data

US 2010/0267657 A1    Oct. 21, 2010

Related U.S. Application Data

(60) Provisional application No. 61/170,344, filed on Apr. 17, 2009.

(51) Int. Cl.
*A61K 31/7068* (2006.01)
*C07H 19/12* (2006.01)
*A61K 31/7028* (2006.01)

(52) U.S. Cl.
CPC ....... *A61K 31/7028* (2013.01); *A61K 31/7068* (2013.01); *C07H 19/12* (2013.01)

(58) Field of Classification Search
None
See application file for complete search history.

(56) References Cited

U.S. PATENT DOCUMENTS

| 5,919,643 A * | 7/1999 | Kelley et al. ............... 435/19 |
| 2003/0229004 A1* | 12/2003 | Zarling et al. ............... 514/1 |
| 2006/0074046 A1* | 4/2006 | Redkar et al. ............... 514/49 |

OTHER PUBLICATIONS

Fortini et al., Cancer Research, 1993, 53, 1149-1155.*
Ruiz et al., Pharm World Sci., 1994, 16(2), 104-112.*
Palii et al., Molecular and Cellular Biology, 2008, 28(2), 752-771.*
Bulgar et al., "Abstract #5547: Enhancement of decitabine cytotoxicity by methoxyamine via inhibition of base excision repair" AACR Annual Meeting—Apr. 18-22, 2009 pp. 1-4.*

* cited by examiner

*Primary Examiner* — Eric Olson
(74) *Attorney, Agent, or Firm* — Tarolli, Sundheim, Covell & Tummino LLP

(57) ABSTRACT

A method treating cancer in a subject comprises administering to the subject a therapeutically effective amount of an antimetabolite agent that induces formation of AP sites in cancer cells of the subjects and an amount AP endonuclease inhibitor effective to potentiate the cytotoxicity of the antimetabolite agent to the cancer cells.

18 Claims, 6 Drawing Sheets

ANTIMETABOLITE AGENT COMBINATIONS IN THE TREATMENT OF CANCER

RELATED APPLICATION

This application claims priority from U.S. Provisional Application No. 61/170,344, filed Apr. 17, 2009, this application also claims priority to U.S. patent application Ser. No. 10/505,400, filed Aug. 19, 2004, (now U.S. Pat. No. 8,324, 282), which is a National Phase Filing of PCT/US2003/ 005032, filed Feb. 19, 2003, the subject matter of which are incorporated herein by reference in their entirety.

FIELD OF THE INVENTION

The present invention relates generally to compounds and methods for treating neoplastic disorders in a subject, and more particularly relates to the use of antimetabolite antineoplastic agents and base excision repair inhibitors in the treatment of certain cancer and/or solid tumors in a subject.

BACKGROUND

Cancer is a worldwide problem. Finding novel compositions and methods for the treatment of cancer is of vital interest. The treatment of cancer falls into three general categories: chemotherapy, radiation therapy and surgery. Often, therapies are combined since a combination of therapies often increases the probability the cancer will be eradicated as compared to treatment strategies utilizing a single therapy. Typically, the surgical excision of large tumor masses is followed by chemotherapy and/or radiation therapy.

Chemotherapeutic agents can work in a number of ways. For example, chemotherapeutics can work by interfering with cell cycle progression or by generating DNA strand breaks. If the cancer cell is not able to overcome the cell cycle blockage or cell injury caused by the therapeutic compound, the cell will often die via apoptotic mechanisms. The use of a single chemotherapeutic agent in the treatment of cancer, with or without surgery or radiation, has several disadvantages. Commonly, cancer cells develop resistance to the chemotherapeutic agent. Such resistance results either in the requirement for higher dosages of the drug and/or the renewed spread of the cancer. Chemotherapeutic agents can be toxic to the patient. Therefore, there is a practical upper limit to the amount that a patient can receive. However, if a second agent can be developed to inhibit the pathway causing resistance, cancer cells may become susceptible to the effects of the chemotherapeutic agent.

The design of a drug to overcome resistance to the chemotherapeutic treatment of cancer should be approached with the goals of 1) finding a combination that reverses resistance and not merely improves the activity of the chemotherapeutic with respect to activity on the tumor, and 2) finding a second drug that does not potentiate the toxic effects of the first chemotherapeutic agent. These conditions require a great deal of empirical testing of agents known to have anticancer properties with agents that either may have anticancer properties, or that may augment the first agent in other ways. Unfortunately, such approaches have thus far proven largely unsuccessful for combinations of many anticancer agents.

Therefore, there exist insufficient therapies that reverse resistance to chemotherapy for the treatment of cancer.

SUMMARY OF THE INVENTION

The present invention relates to compositions and methods useful in the treatment of certain cancers. In part, this application is based on the heretofore unknown recognition that certain molecules that target abasic lesions or AP (apurinic/apyrimidinic) sites in DNA improve, augment, or potentiate the efficacy of antimetabolite antineoplastic agents. In other embodiments, an inhibitor of the base excision pathway, such as an AP endonuclease inhibitor (e.g., methoxyamine), is combined with an antimetabolite antineoplastic agent. An antimetabolite antineoplastic agent is a chemotherapeutic with a similar structure to a substance (a metabolite) required for normal biochemical reactions, yet different enough to interfere with the normal functions of cells, including cell division.

In an aspect of the invention, a method of treating cancer in a subject includes administering to the subject a therapeutically effective amount of an antimetabolite agent that induces formation of AP sites in cancer cells of the subject and an amount AP endonuclease inhibitor effective to potentiate the cytotoxicity of the antimetabolite agent to the cancer cells. The AP endonuclease inhibitor can be selected from group consisting of methoxyamine, O-benzylhydroxylamine; ethyl aminooxyacetate; aminooxyacetic acid; ethyl aminooxyacetate; $H_2NOCHMeCO_2H$; carboxymethoxyamine; aminooxyacetic acid; $HN=C(NH_2)SCH_2CH_2ONH_2$; $H_2NO(CH_2)_3SC(NH_2)=NH$; $MeOC(O)CH(NH_2)CH_2ONH_2$; $H_2NOCH_2CH(NH_2)CO_2H$; canaline; $H_2NO(CH_2)_4ONH_2$; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene)dihydroxylamine; O,O'-(p-phenylenedimethylene)dihydroxylamine; $H_2C=CHCH_2ONH_2$; $H_2NO(CH_2)_4ONH_2$; $H_3C-(CH_2)_{15}-O-NH_2$, 2,2'-(1,2-ethanediyl)bis(3-aminooxy)butenedioic acid dimethyl diethyl ester;

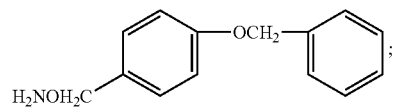

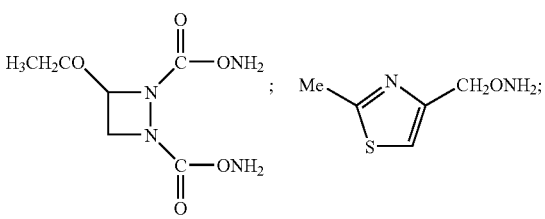

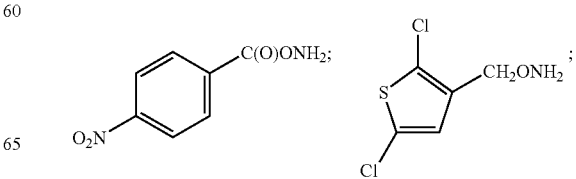

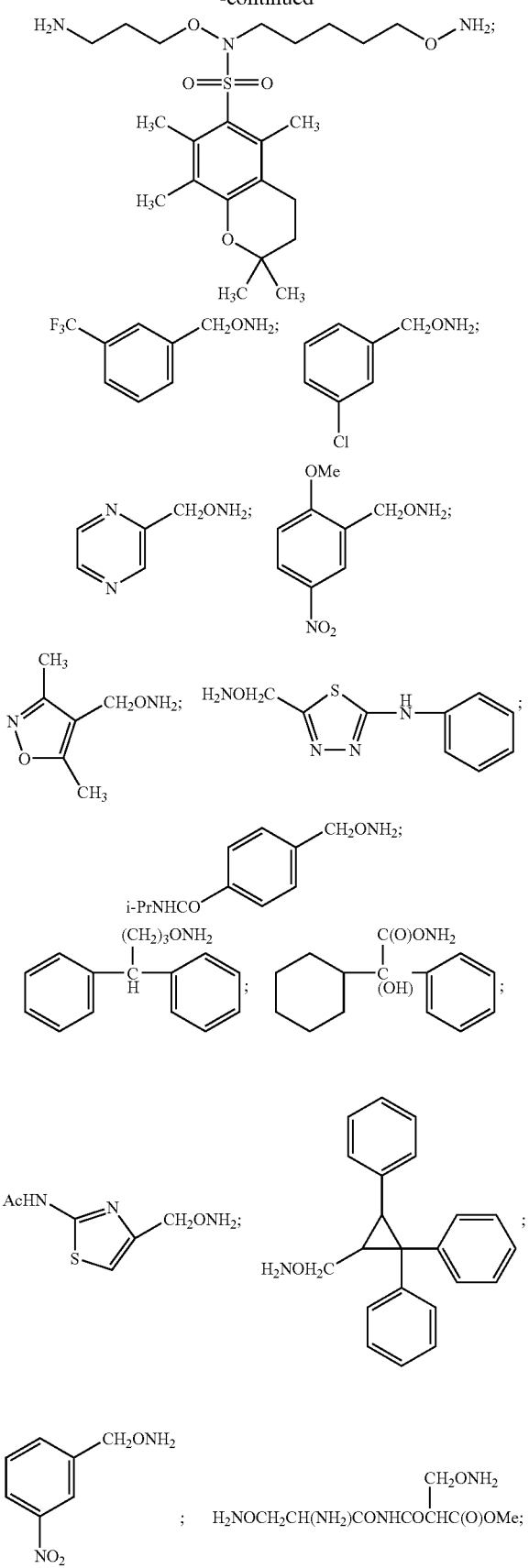

a compound having a structure of Formula I:

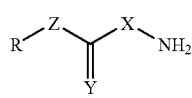

Formula I wherein X is O or NH,
Y is O, S, or NH,
Z is absent or represents O, S, or NH, and
R represents a hydrogen or a hydrocarbon moiety,
and pharmaceutically acceptable salts thereof. In further aspect, the AP endonuclease inhibitor can be methoxyamine.

The antimetabolite agent can include a nucleoside analog. The nucleoside analog can be a hypomethylating agent and include, for example, 5-aza-2'-deoxycytidine.

An anticancer agent can also be administered to the subject in combination with the antimetabolite agent and the AP endonuclease inhibitor. The anticancer agent can include an alkylating agent. An example of an alkylating agent is temozolomide (TMZ).

The amount of antimetabolite agent administered to the subject can be subtherapeutic when administered in the absence of the AP endonuclease inhibitor. The amount of the AP endonuclease inhibitor administered to the subject can also be an amount sufficient to sensitize the cancer cells without causing undue sensitization of normal cells.

The subject to which the antimetabolite agent and the AP endonuclease inhibitor are administered can be selected as having a cancer at least partially resistant to treatment with antimetabolite agent alone. The AP endonuclease inhibitor can be administered in an amount effective to potentiate the activity of the antimetabolite agent and overcome the resistance.

The cancer can be selected from the group consisting of carcinomas, melanomas, sarcomas, lymphomas, leukemias, astrocytomas, gliomas, malignant melanomas, chronic lymphocytic leukemia, lung cancers, colorectal cancers, ovarian cancers, pancreatic cancers, renal cancers, endometrial cancers, gastric cancers, liver cancers, head and neck cancers, and breast cancers.

DETAILED DESCRIPTION

Definitions

Figure 1A:
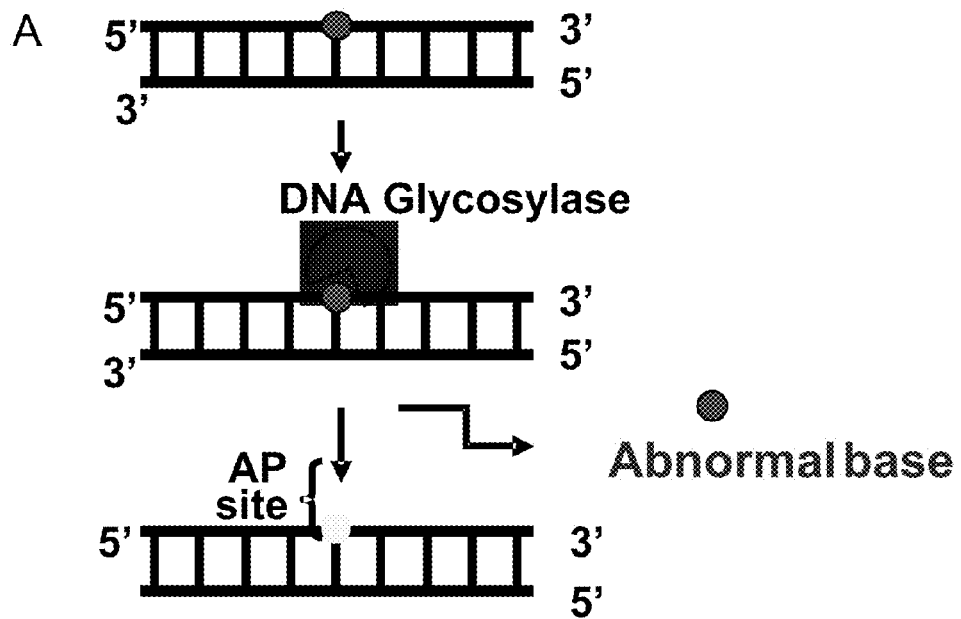
FIGS. 1A-B illustrate a schematic illustrations of (A) DNA repair mechanisms on DNA damage produced by an antimetabolite agent in accordance with an aspect of the invention, and (B) the use of methoxyamine in inhibiting the repair mechanism.

Unless indicated otherwise, the following terms have the following meanings when used herein and in the appended claims. Those terms that are not defined below or elsewhere in the specification shall have their art-recognized meaning.

The term "agent" and "drug" are used herein to mean chemical compounds, mixtures of chemical compounds, biological macromolecules, or extracts made from biological materials, such as bacteria, plants, fungi, or animal particularly mammalian) cells or tissues that are suspected of having therapeutic properties. The agent or drug may be purified, substantially purified, or partially purified.

The term "antimetabolite" is used herein to mean a chemotherapeutic with a similar structure to a substance (a metabolite e.g., nucleoside) required for normal biochemical reactions, yet different enough to interfere with the normal functions of cells, including cell division.

The term "antineoplastic" is used herein to mean a chemotherapeutic intended to inhibit or prevent the maturation and proliferation of neoplasms (tumors) that may become malignant, by targeting the DNA.

The term "staining" is used herein to mean any number of processes known to those in the field that are used to better visualize, distinguish or identify a specific component(s) and/or feature(s) of a cell or cells.

The term "in operable combination", "in operable order" and "operably linked" is used herein to mean the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "morphology" is used herein to mean the visual appearance of a cell or organism when viewed with the eye, a light microscope, a confocal microscope or an electron microscope, as appropriate.

The term "subject," "individual," and "patient" are used interchangeably herein to mean a human or other animal, such as farm animals or laboratory animals (e.g., guinea pig or mice) capable of having cell cycle (influenced) determined diseases, either naturally occurring or induced, including but not limited to cancer.

The term "reverses resistance" means that the use of a second agent in combination with a primary chemotherapeutic is able to produce a significant decrease in tumor volume at a level of statistical significance (e.g., $p<0.05$) when compared to tumor volume of untreated tumor in the circumstance where the primary chemotherapeutic alone is unable to produce a statistically significant decrease in tumor volume compared to tumor volume of untreated tumor. This generally applies to tumor volume measurements made at a time when the untreated tumor is growing log rhythmically.

The term "potentiate" as used herein means to enhance or increase the beneficial activity or efficacy of the anticancer agent over that which would be expected from the anticancer agent alone or the potentiating agent alone.

The term "sensitize" as used herein means to alter cancer cells or tumor cells in a way that allows for more effective treatment of the associated neoplastic disease with an antimetabolite agent, an anticancer agent, or radiation therapy. In some embodiments, normal cells are not affected to an extent that causes the normal cells to be unduly injured by the antimetabolite, chemotherapy, or radiation therapy.

The term "synergistic effect" as used herein means the combined effect of two or more anticancer agents or chemotherapy drugs can be greater than the sum of the separate effects of the anticancer agents or chemotherapy drugs alone. For example, the combined effect of a BER inhibitor, such as methoxyamine, and an antimetabolite agent, such as decitabine, can be greater than the sum of the separate effects of methoxyamine and decitabine alone.

The term "therapeutically effective amount" means the amount of the subject compound that will elicit a desired response, for example, a biological or medical response of a tissue, system, animal, or human that is sought, for example, by a researcher, veterinarian, medical doctor, or other clinician.

The term "wild type" (wt) cell or cell line is used herein, for purposes of the specification and claims, to mean a cell or cell line that retains the characteristics normally associated with that type of cell or cell line for the physiological process or morphological characteristic that is being examined. It is permissible for the cell or cell line to have non-wild type characteristics for physiological process or morphological characteristics that are not being examined as long as they do not appreciably affect the process or characteristic being examined.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

The term "small molecule" refers to a low molecular weight organic compound, which is by definition not a polymer. The small molecule can bind with high affinity to a biopolymer, such as protein, nucleic acid, or polysaccharide and in some instances alter the activity or function of the biopolymer. The upper molecular weight limit for a small molecule is about 800 Daltons, which allows for the possibility to rapidly diffuse across cell membranes so that they can reach intracellular sites of action. In addition, this molecular weight cutoff can be a condition for oral bioavailability.

The term "analog" refers to a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (The Science and Practice of Pharmacology, 19th Edition (1995), chapter 28).

The term "derivative" refers to a substance related to a base structure, and theoretically derivable from the base structure.

The term "mimetic" refers to a biomolecule that mimics the activity of another biologically active molecule.

The present invention relates to compositions and methods of treating cancer in subject by administering to the subject a first formulation comprising an antimetabolite antineoplastic agent that induces formation of AP sites in cancer cells of the subject and a second formulation comprising an AP endonuclease inhibitor that is effective to potentiate the cytotoxicity of the antimetabolite agent to the cancer cells.

Injury to DNA is minimized by enzymes that recognize errors, remove them, and replace the damaged DNA with corrected nucleotides. DNA damage occurs when a single-strand break is introduced, a base is removed leaving its former partner unpaired, a base is covalently modified, a base is converted into another that is not appropriately paired with the partner base, or a covalent link is introduced between bases on opposite strands. Excision repair systems remove the mispaired or damaged base from the DNA strand and then synthesize new DNA to replace it. Base excision repair (BER) is initiated during replication of DNA and allows for correction of damaged bases/mispaired bases prior to completion of replication.

Base excision repair (BER) is initiated by a DNA glycosylase that removes N-glycosidic (base-sugar) bonds, liberating the damaged base and generating an abasic site (e.g., an apurinic or apyrimidinic (AP) site). An apurinic or apyrimidinic (AP) site results from the loss of a purine or pyrimidine residue, respectively, from DNA (deoxyribonucleic acid). Uracil residues can form from the spontaneous deamination of cytosine and can lead to a C→T transition if unrepaired. There is also a glycosylase that recognizes and excises hypoxanthine, the deamination product of adenine. Other glycosylases remove alkylated bases (such as 3-methyladenine, 3-methylguanine, and 7-methylguanine), ring-opened purines, oxidatively damaged bases, and in some organisms, UV photodimers.

The AP site is further processed by a 5'-3' endonuclease (AP endonuclease (APE)) that incises the phosphodiester bond on both sides of the damaged purine or pyrimidine base. The AP endonucleases introduce chain breaks by cleaving the phosphodiester bonds at the AP sites.

PARP aids in processing of DNA strand breaks induced during BER. PARP is a DNA nick surveillance protein that binds weakly to BER intermediates when single-nucleotide BER proceeds normally to completion. In contrast, when single nucleotide BER is stalled by a block in the excision step, PARP binds strongly to the BER intermediate, along with AP endonuclease (APE), DNA pol β, and FEN-1.

In mammalian cells, the 5'-deoxyribose sugar phosphate is removed by the intrinsic AP lyase (dRP) activity of DNA polymerase β (pol β). DNA polymerase enzyme also fills the gaps with new nucleotides.

Finally, DNA ligase covalently links the 3' end of the new material to the old material. Thus, the wild-type sequence is restored.

Topoisomerases I and II are also involved in DNA repair, as they recognize spontaneous AP sites and form stable cleavable complexes. Topoisomerase II inhibitors promote DNA cleavage and other chromosomal aberrations, including sister chromatid exchanges.

Figure 1B:
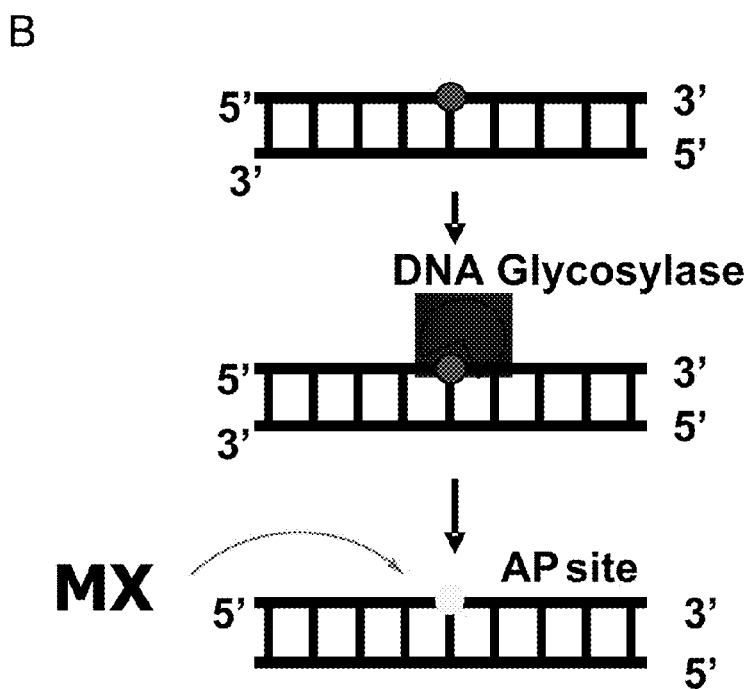

The antimetabolite antineoplastic agents (or antimetabolite agents) in accordance with the present invention are agent compounds, or small molecules that interfere with the replication, translation or transcription of nucleic acids and induce formation of AP sites in cancer cells of a subject. In one embodiment of the present invention, the antimetabolite agent can include a nucleoside analog that when administered to a cancer cell of a subject induces formation of AP sites in the cancer cells. Nucleoside analogs are antimetabolites that mimic nucleosides. FIG. 1 illustrates that antimetabolite nucleoside analogs incorporated into DNA are recognized and processed by the base excision repair (BER) pathway and induce formation of AP sites. The inhibition of the BER pathway with an AP endonuclease inhibitor (e.g., methoxyamine (mx)) can potentiate the cytoxic effects of the nucleoside analog administered to cancer cells.

One example of a nucleoside analog that is an antimetabolite and induces formation of an AP site is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, can cause serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381. Further 5-FU derivatives have been described in the following patents listed in JP 50-50383, JP 50-50384, JP 50-64281, JP 51-146482, and JP 53-84981 hereby individually incorporated by reference herein.

In some embodiments of the invention, the nucleoside analog that induces formation of AP sites in cancer cells of the subject can be a hypomethylating agent. As used herein, the term "hypomethylating agent" refers to an agent that reduces or reverses DNA methylation, either at a specific site (e.g., a specific CpG island) or generally throughout a genome. Hypomethylating agents can be referred to as possessing "hypomethylating activity." By way of example, such activity is measured by determining the methylation state and/or level of a specific DNA molecule or site therein, or the general methylation state of a cell, on parallel samples that have and have not been treated with the hypomethylating agent (or putative hypomethylation agent). A reduction in methylation in the treated (versus the untreated) sample indicates that the agent has hypomethylating activity.

An example of a nucleoside analog that is a hypomethylating agent is 4-amino-1-(2-deoxy-b-D-erythro-pentofuranosyl)-1,3,5-triazin-2(1H)-one (e.g., 5-aza-2'-deoxycytidine, decitabine, or DACOGEN, Eisai Inc., Woodcliff Lake, N.J.). Decitabine is an antagonist of its related natural nucleoside, deoxycytidine. The only structural difference between these two compounds is the presence of a nitrogen at position 5 of the cytosine ring in decitabine as compared to a carbon at this position for deoxycytidine. Two isomeric forms of decitabine can be distinguished. The β-anomer is the active form. The modes of decomposition of decitabine in aqueous solution are (a) conversion of the active β-anomer to the inactive .alpha.-anomer (Pompon et al. (1987) J. Chromat. 388:113-122); (b) ring cleavage of the aza-pyrimidine ring to form N-(formylamidino)-N'—.beta.-D-2'-deoxy (ribofuranosy)-urea (Mojaverian and Repta (1984) J. Pharm. Pharmacol. 36:728-733); and (c) subsequent forming of guanidine compounds (Kissinger and Stemm (1986) J. Chromat. 353:309-318).

Decitabine possesses multiple pharmacological characteristics. At a molecular level, it is S-phase dependent for incorporation into DNA. At a cellular level, decitabine can induce cell differentiation and exert hematological toxicity. Despite having a short half life in vivo, decitabine has excellent tissue distribution.

The most prominent function of decitabine is its ability to specifically and potently inhibit DNA methylation. As described above for methylation of cytosine in CpG islands as an example, methylation of cytosine to 5-methylcytosine occurs at the level of DNA. Inside the cell, decitabine is first converted into its active form, the phosphorylated 5-aza-deoxycytidine, by deoxycytidine kinase, which is primarily synthesized during the S phase of the cell cycle. The affinity of decitabine for the catalytical site of deoxycytidine kinase is similar to the natural substrate, deoxycytidine. Momparler et al. (1985) 30:287-299. After conversion to its triphosphate form by deoxycytidine kinase, decitabine is incorporated into replicating DNA at a rate similar to that of the natural substrate, dCTP. Bouchard and Momparler (1983) Mol. Pharmacol. 24:109-114.

Incorporation of decitabine into the DNA strand has a hypomethylation effect. Each class of differentiated cells has its own distinct methylation pattern. After chromosomal duplication, in order to conserve this pattern of methylation, the 5-methylcytosine on the parental strand serves to direct methylation on the complementary daughter DNA strand. Substituting the carbon at the 5 position of the cytosine for a nitrogen interferes with this normal process of DNA methylation. The replacement of 5-methylcytosine with decitabine at a specific site of methylation produces an irreversible inactivation of DNA methyltransferase, presumably due to formation of a covalent bond between the enzyme and decitabine. Juttermann et al. (1994) Proc. Natl. Acad. Sci. USA 91:11797-11801. By specifically inhibiting DNA methyltransferase, the enzyme required for methylation, the aberrant methylation of the tumor suppressor genes can be prevented. Moreover, once decitabine is incorporated into the DNA strand, the BER pathway is activated and formation of the AP site is induced.

Other examples, of nucleoside analogs that can be used to treat cancer are listed in U.S. Pat. No. 4,000,137, which is incorporated herein by reference. U.S. Pat. No. 4,000,137 discloses that the peroxidative oxidation product of inosine, adenosine, or cytidine with methanol or ethanol has activity against lymphocytic leukemia. Cytosine arabinoside (also referred to as Cytarabin, araC, and Cytosar) is a nucleoside analog of deoxycytidine that was first synthesized in 1950 and introduced into clinical medicine in 1963. The primary action of araC is inhibition of nuclear DNA synthesis. Handschumacher, R. and Cheng, Y., "Purine and Pyrimidine Antimetabolites", Cancer Medicine, Chapter XV-1, 3rd Edition, Edited by J. Holland, et al., Lea and Febigol, publishers. 5-Azacytidine (VIDAZA, Celegene Corp., Summit, N.J.) is a cytidine analog that is primarily used in the treatment of acute myelocytic leukemia and myelodysplastic syndrome.

In some embodiments of the invention, the antimetabolite agent can be selected from the group consisting of 5-Fu, 5-aza-deoxycytidine, and 5-azacytidine. In another embodiment, the antimetabolite agent can be decitabine and pharmaceutically acceptable salts thereof. For example, the decitabine can be the disodium salt.

The AP endonuclease inhibitor that potentiates the cytotoxicity of the antimetabolite agent can be a small molecule compound with a primary amine group that forms a covalent linkage with and/or binds to an aldehyde group of an AP site induced by the antimetabolic agent. In single-nucleotide BER, the deoxyribose phosphate (dRP) in the abasic site is removed by the lyase activity of DNA pol β. Binding of the AP endonuclease inhibitor to an aldehyde group can structurally alter the AP site so that AP endonuclease does not recognize the modified AP site and/or prevent AP endonuclease-mediated cleavage of phosphodiester bonds, thus blocking single nucleotide BER.

In an aspect of the invention, the reaction of the AP endonuclease inhibitor with the aldehyde group in the cancer cells can be faster than AP endonuclease to inhibit repair of DNA. Advantageously, administration of the AP endonuclease inhibitor in combination with the antimetabolite agent to tumor cells can bypass other resistance factors, such as MMR defects and high MGMT activity in the tumor cells.

In some embodiments, the AP endonuclease inhibitor can be an aminooxy small molecule compound that can react with an AP site faster than AP endonuclease. One example of an aminooxy compound that that can react with an AP site faster than AP endonuclease is methoxyamine (MX) or salts thereof. Methoxyamine when administered in combination with an antimetabolite agent, such as decitabine, to a subject with cancer can potentiate the anticancer effect of the antimetabolite agent without additive systemic toxicity.

In other embodiments the AP endonuclease inhibitor can be a small molecule having the formula I:

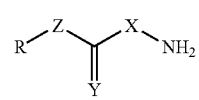

Formula I wherein X is O or NH,

Y is O, S, or NH,

Z is absent or represents O, S, or NH,

R represents a hydrogen or a hydrocarbon moiety, and pharmaceutically acceptable salts thereof.

Other examples of small molecules primary amine compounds that can bind to AP sites and prevent APE-mediated cleavage of phosphodiester bonds include O-benzylhydroxylamine; ethyl aminooxyacetate; aminooxyacetic acid; ethyl aminooxyacetate; $H_2N-OCHMeCO_2H$; carboxymethoxyamine; aminooxyacetic acid; $HN=C(NH_2)SCH_2CH_2ONH_2$; $H_2N-O(CH_2)_3SC(NH_2)=NH$; $MeOC(O)CH(NH_2)CH_2O-NH_2$; $H_2NOCH_2CH(NH_2)CO_2H$; canaline; $H_2N-O(CH_2)_4O-NH_2$; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene)dihydroxylamine; O,O'-(p-phenylenedimethylene)dihydroxylamine; $H_2C=CHCH_2O-NH_2$; $H_2N-O(CH_2)_4O-NH_2$; $H_3C(CH_2)_{15}O-NH_2$, 2,2'-(1,2-ethanediyl)bis(3-aminooxy)butenedioic acid dimethyl diethyl ester; compounds having any of the following structures:

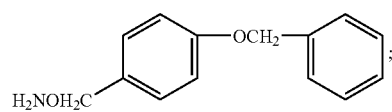

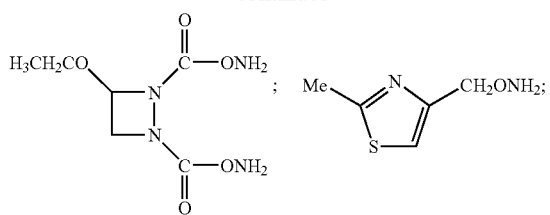
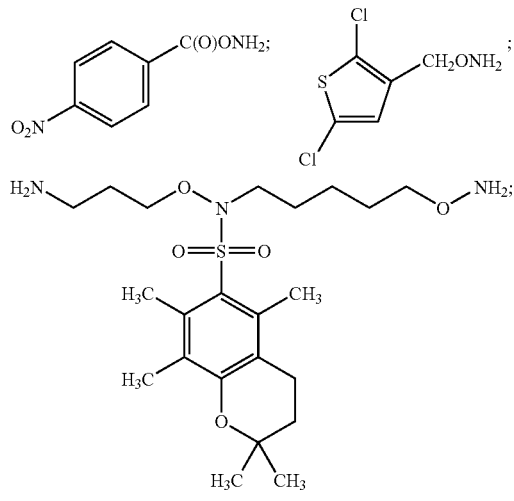
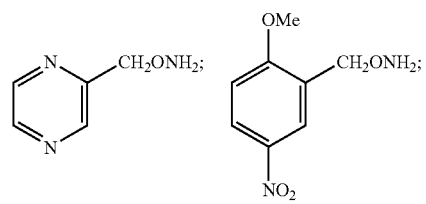
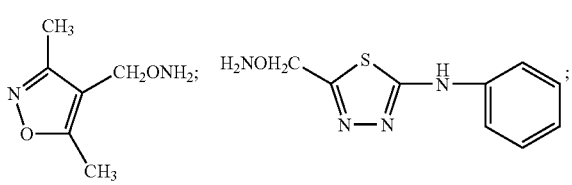
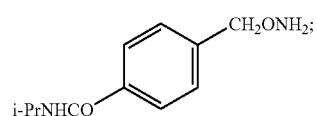
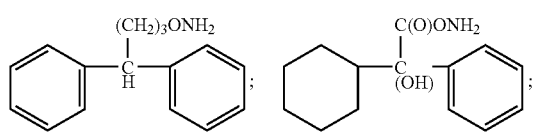
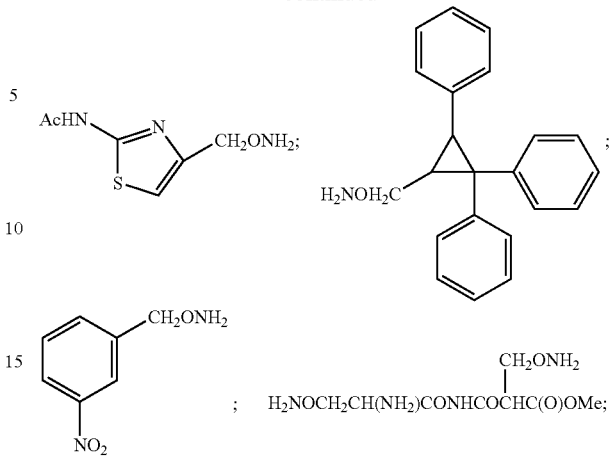

and pharmaceutically acceptable salts of any of these compounds.

Still other examples of small molecules primary amine compounds that can bind to AP sites and prevent APE-mediated cleavage of phosphodiester bonds can be identified using a high-throughput screening assay described below. The high-throughput screening assay includes two molecular reaction assays:

1. Analysis of chemical-modified AP Sites assayed by Aldehyde Reactive Probe (ARP). This is a competitive assay to measure the reactivity with AP site between ARP reagent (Dojindo Molecular Technologies Inc., Gaithersburg, Md.) and the screening compounds. ARP and MX have a similar reactivity with AP sites. They react specifically with an aldehyde group that is open ring form of the AP sites. Thus, this assay will allow identification of compounds with potential to block AP site repair based on the binding affinity and efficiency to AP sites of screening compounds compared to ARP and MX.

a. AP site standard preparation: AP sites were produced in a calf thymus DNA by heat/acid-buffer solution. Intact calf thymus DNA was added to sodium citrate buffer (10 mM sodium citrate containing 10 mM NaH.sub.2PO.sub.4 and 10 mM NaCl, pH 5.0) and held at 70° C. for 30 min. The reaction was stopped by chilling rapidly on ice, and the DNA was then precipitated with cold ethanol, washed with 70% ethanol, dried, and resuspended in sterilized distilled water.

b. AP-DNA (15 pg) was incubated with test compounds at different concentrations at 37° C. for 30 min prior to ARP (1 mM) or ARP alone (Dojindo Molecular Technologies Inc., Gaithersburg, Md.) for 30 min. After precipitation and wash with ethanol, DNA was resuspended in TE buffer (10 mM Tris-HCl, 1 mM EDTA, pH 7.2). DNA was heat-denatured at 100° C. for 5 min, quickly chilled on ice, and mixed with an equal amount of 2 M ammonium acetate. The single-stranded DNA was then immobilized on a BAS-85 NC membrane (Schleicher and Schuell) using a vacuum filter device (Schleicher and Schuell). The NC membrane was incubated with streptavidinconjugated horseradish peroxidase (BioGenix) at room temperature for 30 min. After NC membrane was rinsed with washing buffer containing NaCl (0.26 M), EDTA (1 mM), Tris-HCl (20 mM), and Tween 20 (1%), ARP-AP sites are visualized with ECL reagents (Amersham Corp.) and quantitated by scanning densitometer.

2. AP sites cleavaged by AP-endonuclease (APE). This assay confirms that AP sites modified by potential BER inhibitors are resistant to cleavage by APE, (Trevigen, Gaithersburg, Md.) a BER protein. The assay may be performed as follows (see also FIGS. 23A and B):

a. AP site is prepared by replacing single nucleoside with deoxyuridine in duplex oligonucleotides (40 mer).

b. Regular AP site is produced in the duplex oligonucleotides by human uracil DNA glycosylase (LIDGase, Trevigen, Gaithersburg, Md.) to remove the uracil residue.

c. To generate MX-adducted AP site substrates: the UDG-treated duplex oligonucleotides are mixed with 10 mM MX in buffer containing 10 mM KPO4, pH 7.1 and incubated at 37° C. After 30 min, the substrates are recovered by ethanol precipitation, lyophilized, resuspended in water, and stored at −20 C.

d. APE-cleavage reaction: DNA substrates containing either regular AP-sites or chemical modified AP sites are incubated with APE (Trevigen, Gaithersburg, Md.) for 30 min and reactants are precipitated with 100% cold ethanol, washed with 70% ethanol and resuspended in TE buffer. The reactants are resolved by denaturing 20% polyacrylamide gel electrophoresis and visualized by silver staining (Silver Staining Kit, Pharmacia Biotech).

In some embodiments, the antimetabolite administered in combination with the AP endonuclease inhibitor inhibitor can be used to treat a patient or subject having a neoplastic disease. For example, the neoplastic disease can be a cancer selected from the group consisting of carcinomas, melanomas, sarcomas, lymphomas, leukemias, astrocytomas, gliomas, malignant melanomas, chronic lymphocytic leukemia, lung cancers, prostate cancer, colorectal cancers, ovarian cancers, pancreatic cancers, renal cancers, endometrial cancers, gastric cancers, liver cancers, head and neck cancers.

In some embodiments, the antimetabolite agent and the AP endonuclease inhibitor can be administered to an individual in combination. For example, the AP endonuclease inhibitor and the antimetabolite agent can be administered to an individual together in a parenteral formulation. Alternatively, the AP endonuclease inhibitor and the antimetabolite agent can be administered to an individual together in an oral formulation, such as a solid dosage formulation.

In some embodiments, the AP endonuclease inhibitor and the antimetabolite agent can be administered to an individual sequentially, where the individual is first given the antimetabolite agent and then given the AP endonuclease inhibitor. For example, the individual can be given the antimetabolite agent in a parenteral formulation, such as an intravenous formulation, or an oral formulation, such as a solid dosage formulation and then given the AP endonuclease inhibitor in a parenteral formulation, such as an intravenous formulation, or an oral formulation, such as a solid dosage formulation.

Alternatively, in some embodiments, the AP endonuclease inhibitor and the antimetabolite agent can be administered to an individual sequentially, where the individual is first given the AP endonuclease inhibitor and then given the antimetabolite agent. For example, the individual can be given the AP endonuclease inhibitor in a parenteral formulation, such as an intravenous formulation, or an oral formulation, such as a solid dosage formulation and then given the antimetabolite agent in a parenteral formulation, such as an intravenous formulation, or an oral formulation, such as a solid dosage formulation.

In some embodiments, the antimetabolite agent and the AP endonuclease inhibitor can create an anticancer effect greater than that of the separate anticancer effects of the individual agents. For example, the combined anticancer effect of the antimetabolite agent and the AP endonuclease inhibitor can be greater than the added anticancer effect of the antimetabolite agent and the AP endonuclease inhibitor when used individually.

In certain embodiments, the present invention contemplates the use of an antimetabolite agent, such as decitabine, that induces the formation of AP sites and an AP endonuclease inhibitor, such as methoxyamine.

In some embodiments, the antimetabolite agent can be administered in a dose of from about 10 mg/m$^2$ to about 5,000 mg/m$^2$ body surface area. For example, the dose can be from about 20 mg/m$^2$ to about 200 mg/m$^2$ body surface area; the dose can be from about 150 mg/m$^2$ to about 500 mg/m$^2$ body surface area; the dose can be from about 400 mg/m$^2$ to about 1000 mg/m$^2$ body surface area; the dose can be from about 900 mg/m$^2$ to about 5,000 mg/m$^2$ body surface area; the dose can be from about 200 mg/m$^2$ to about 1,000 mg/m$^2$ body surface area; or the dose can be from about 500 mg/m$^2$ to about 600 mg/m$^2$ body surface area. In some embodiments, the antimetabolite agent can be decitabine and pharmaceutically acceptable salts thereof.

In some embodiments, the ratio of AP endonuclease inhibitor to antimetabolite agent can be from about 1 to about 1:10000. For example, ratio of AP endonuclease inhibitor to antimetabolite agent can be from about 1:2 to about 1:100; the ratio of AP endonuclease inhibitor to antimetabolite agent can be from about 1:50 to about 1:500; the ratio of AP endonuclease inhibitor to antimetabolite agent can be from about 1:450 to about 1:10000; the ratio of AP endonuclease inhibitor to antimetabolite agent can be from about 1:5 to about 1:500; the ratio of AP endonuclease inhibitor to antimetabolite agent can be from about 1:10 to about 1:50; the ratio of AP endonuclease inhibitor to antimetabolite agent can be from about 1:15 to about 1:40; or the ratio of AP endonuclease inhibitor to antimetabolite agent can be from about 1:20 to about 1:30.

In some embodiments, an AP endonuclease inhibitor is administered in an amount sufficient to enhance or increase the effect of an antimetabolite agent.

Some embodiments provide a method of treating cancer, comprising providing a first formulation containing an antimetabolite agent and a second formulation containing an AP endonuclease inhibitor that can be administered separately or as a combined formulation selecting a subject diagnosed with cancer, wherein the cancer is resistant to treatment with the antimetabolite agent alone or in combination with other anticancer agents; administering said first formulation and said second formulation; wherein the amount of the first formulation and the amount of the second formulation can be in a amount that when administered to said subject the anticancer effect can be greater than the anticancer effect of the first formulation alone.

In other embodiments, the AP endonuclease inhibitor and the antimetabolite agent can be administered to subject in combination with at least one other BER inhibitor. In an aspect of the invention, the at least one other BER inhibitor can include a PARP inhibitor. Examples of PARP inhibitors are 4-amino-1,8-naphthalimide (ANI), PD128763, 3-AB, 6-AN, and 8-hydroxy-2-methyl-quinazolin-4-[$^3$H]one (NU-1025).

Other examples of BER inhibitors that can be administered to the subject in combination with the antimetabolite agent and the AP endonuclease inhibitor include DNA polymerase inhibitors (e.g., DNA polymerase β, γ or ε), such as prunasin, aphidicolin, 2',3'-dideoxycytidine triphosphate (ddCTP), 2',3'-dideoxythymidine triphosphate (ddTTP), 2',3'-dideoxyadenosine triphosphate (ddATP), 2',3'-dideoxyguanosine triphosphate (ddGTP), 1-beta-D-arabinofuranosylcytosine (Ara-C), caffeine, arabinocytidine, and bleomycin.

Still other examples of BER inhibitors that can be administered to the subject in combination with the antimetabolite agent and the AP endonuclease inhibitor include DNA ligase inhibitors (e.g., DNA ligase I, II, or III), such as ursolic and oleanolic acids, aleuritolic acid, protolichesterinic acid, swertifrancheside, fulvoplumierin, fagaronine chloride, and bleomycin. XRCC1 is the protein partner of DNA ligase III, and inhibitors of XRCC1, such as 3-AB, are useful as BER inhibitors as well.

Further examples of BER inhibitors that can be administered to the subject in combination with the antimetabolite agent and the AP endonuclease inhibitor include topoisomerase II inhibitors. Topoisomerase inhibitors induce DNA cleavage and other chromosomal aberrations, including sister chromatid exchanges. Compounds useful as BER inhibitors also include topoisomerase II inhibitors, such as etoposide (VP-16, VP-16-123), meso-4,4'-(2,3-butanediyl)-bis-(2,6-piperazinedione) (ICRF-193, a bisdioxopiperazine), doxorubicin (DOX), L amsacrine (4',9-acridinylaminomethanesulfon-m-anisidide; mAMSA), pazelliptine, nalidixic acid, oxolinic acid, novobiocin, coumermycin A1, fostriecin, teniposide, mitoxantrone, daunorubicin, N-[2-dimethylamino)ethyl]acridine-4-carboxamide (DACA), merbarone, quinacrine, ellipticines, epipodophyllotoxins, ethidium bromide, epirubicin, pirarubicin, 3'-deamino-3'-morpholino-13-deoxo-10-hydroxy caminomycin; 2",3"-bis pentafluorophenoxyacetyl-4',6'-ethylidene-beta-D glucoside of 4'-phosphate-4'-dimethylepipodophyollotoxin 2N-methyl glucamine salt (F11782; a fluorinated lipophilic epipodophylloid), adriamycin, actinomycin D, anthracyclines (such as 9-aminoanthracycline), and pyrazoloacridine (PZA). Topoisomerase I inhibitors, such as camptothecin and topotecan can also be used as BER inhibitors.

In some embodiments, other enzyme inhibitors, whether known in the art or hereafter identified, as well as inhibitors of other elements of the BER pathway, such as DNA alkyltransferase, may be employed in compositions and methods without departing from the scope and spirit of the present embodiments.

In certain embodiments, the present invention contemplates the use of 1) a PARP inhibitor, 2) an antimetabolite agent that induces the formation of AP sites, such as decitabine, and 3) an AP endonuclease inhibitor, such as methoxyamine.

In still other embodiments, the AP endonuclease inhibitor and the antimetabolite agent can be administered to subject in combination with at least one other anticancer agent that induces formation of AP sites. Anticancer agents that induce the formation of AP sites include intercalating agents, such as bleomycin, adriamycin, quinacrine, echinomycin (a quinoxaline antibiotic), and anthrapyrazoles.

Radiation, such as gamma radiation, UVA, and UVB, can be used to generate AP sites according to the methods of the invention. Ultraviolet light is absorbed in DNA with the formation of UV-specific di-pyrimidine photoproducts. Exposure to gamma irradiation, UVA, and UVB can induce damaged pyrimidine photodimers Anticancer agents that induce the formation of AP sites can also include DNA oxidizing agents, such as hydrogen peroxide.

Anticancer agents that induce the formation of AP sites can further include alkylating agents such, as temozolomide (TMZ), 1,3-bis(2-chloroethyl)-1-nitrosourea (BCNU) $MeOSO_2(CH_2)_2$-lexitropsin (Me-Lex), cis-diamminedichloroplatinum II (cisplat; cis-DDP), mitomycin bioreductive alkylating agents, quinones, streptozotocin, cyclophosphamide, nitrogen mustard family members such as chlorambucil, pentostatin (and related purine analogs), fludarabine, bendamustine hydrochloride, chloroethylating nitrosoureas (e.g., lomustine, fotemustine, cystemustine), dacarbazine (DTIC), and procarbazine. In certain embodiments, the alkylating agent is a nitrosoruea, such as a mustine.

Alkylating agents can function by adding methyl groups to DNA, cross-linking macromolecules essential for cell division, and linking guanine bases in DNA through their $N^7$ atoms. Both inter- and intra-strand cross-links can be mediated by alkylating agents. Inter-strand cross-links prevent the separation of the DNA strands necessary for cell division, and by being more difficult to repair, constitute the more lethal lesion.

In certain embodiments, the anticancer agent is selected from radiosensitizers such as 5-iodo-2'-deoxyuridine (IUdR), fludarabine, 6-thioguanine, hypoxanthine, uracil, ecteinascidin-743, and camptothecin and analogs thereof.

In certain embodiments, the anticancer agent is not temozolomide. In certain embodiments, the anticancer agent is not BCNU. In certain embodiments, the anticancer agent is not PE128723, 6-AN, 3-AB, BCNU, or temozolomide It will be appreciated that compositions or formulations provided herein may be in any form, which allows for the composition to be administered to a patient. For example, the composition may be in the form of a solid, liquid or gas (e.g., aerosol). Other routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavemous, intrathecal, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

In another aspect, the present invention relates to a pharmaceutical composition comprising physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents;

coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries, which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.,* 23(3):440-50 (2001)) or hydrogels (Mayer et al., *Opthalmologica,* 210(2):101-3 (1996)); ophthalmic ointments; ophthalmic suspensions, such as microparticulates, drug-containing small polymeric particles that are suspended in a liquid carrier medium (Joshi, A., J. *Ocul. Pharmacol.,* 10(1):29-45 (1994)), lipid-soluble formulations (Alm et al., *Prog. Clin. Biol. Res.,* 312:447-58 (1989)), and microspheres (Mordenti, *Toxicol. Sci.,* 52(1):101-6 (1999)); and ocular inserts. All of the above-mentioned references are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 10 microgram/kg and 100 mg/kg body weight, preferably between about 100 microgram/kg and 10 mg/kg body weight. Alternatively, dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 $mg/m^2$ and 2000 $mg/m^2$ body surface area per day of each active ingredient, typically between 1 $mg/m^2$ and 500 $mg/m^2$ body surface area per day, for example 5 m g/$m^2$ to 200 $mg/m^2$ body surface area per day. In other embodiments, an intravenous, subcutaneous, or intramuscular dose of each active ingredient of between 0.01 $mg/m^2$ and 100 $mg/m^2$ body surface area per day, typically between 0.1 $\mu m^2$ mg and 60 $mg/m^2$ body surface area per day, for example, 1 $mg/m^2$ to 40 $mg/m^2$ body surface area per day can be used. In cases of administration of a pharmaceutically acceptable salt, dosages may be calculated as the free base. In some embodiments, the composition is administered 1 to 4 times per day. Alternatively, the compositions of the invention may be administered by continuous intravenous infusion, preferably at a dose of each active ingredient up to 1000 $mg/m^2$ body surface area per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, typically between 30-90% and most typically between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the L compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

Throughout the specification, any recitation of a particular compound should be understood to encompass that compound and any (other) pharmaceutically acceptable salts thereof.

Generally, the nomenclature used hereafter and the laboratory procedures in cell culture, tissue culture, tumor biology, and molecular genetics described below are those well known and commonly employed in the art. Standard techniques are used for cell culture methods, experimental design and compound formulation and nomenclature. Generally, chemical reactions and purification steps are performed according to the manufacturer's specifications. The techniques and procedures are generally performed according to conventional methods in the art and various general references (see, generally, Sambrook et al. *Molecular Cloning. A Laboratory Manual,* 2d ed. (1989) Cold Spring Harbor Laboratory Press, Cold Spring Harbor, N.Y., and *Current Protocols in Molecular Biology* (1996) John Wiley and Sons, Inc., N.Y., which are incorporated herein by reference) which are provided throughout this document. All the information contained therein is incorporated herein by reference.

EXAMPLES

Enhancement of Decitabine Cytotoxicity by Methoxyamine Via Inhibition of Base Excision Repair Decitabine (5aza-2'deoxycytidine) is a nucleoside analog used for the treatment of hematological malignancies. Previously, it was shown that the cytotoxic effect of low dose decitabine treatment is due to incorporation of its active metabolite, 5aza-2'deoxycytidine triphosphate, into DNA leading to inhibition of DNA methylation by binding irreversibly to DNA methyltransferases. We hypothesized that incorporated 5aza-2'deoxycytidine (or its deaminated analog, 5aza-2'deoxyuridine) into DNA is also recognized and processed by the base excision repair (BER) pathway. In this case, inhibition of BER by methoxyamine (MX) would potentiate the cytotoxicity of decitabine. We evaluated role of BER in decitabine cytotoxicity in colon cancer, melanoma cells, and primary acute myelogenos leukemia (AML) cells.

Figure 2A:
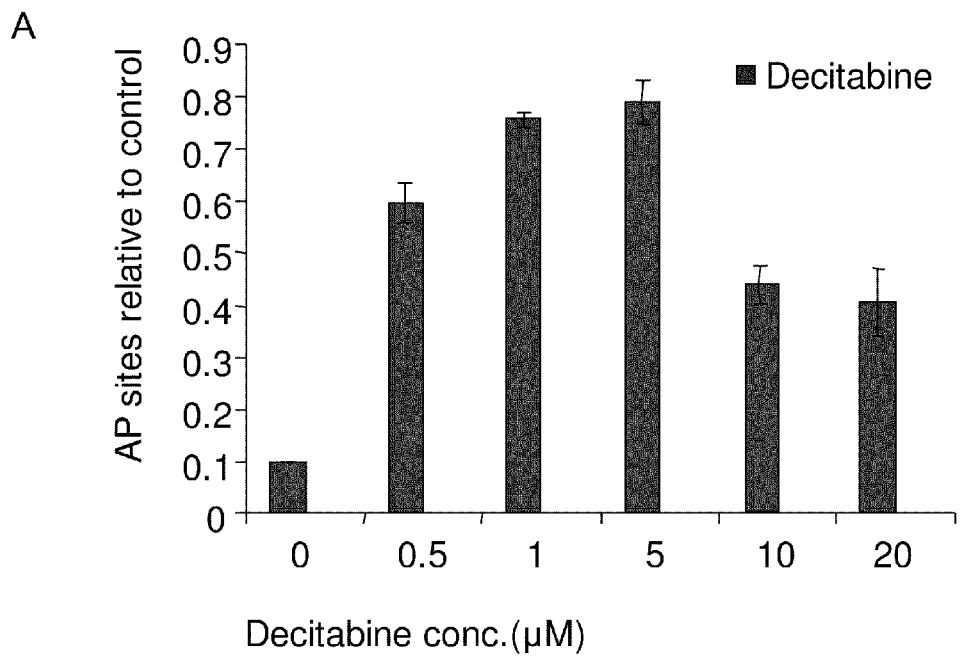
FIGS. 2A-B illustrate charts showing dose and time dependant abasic site formation in cancer cells following decitabine treatment.
Figure 2B:
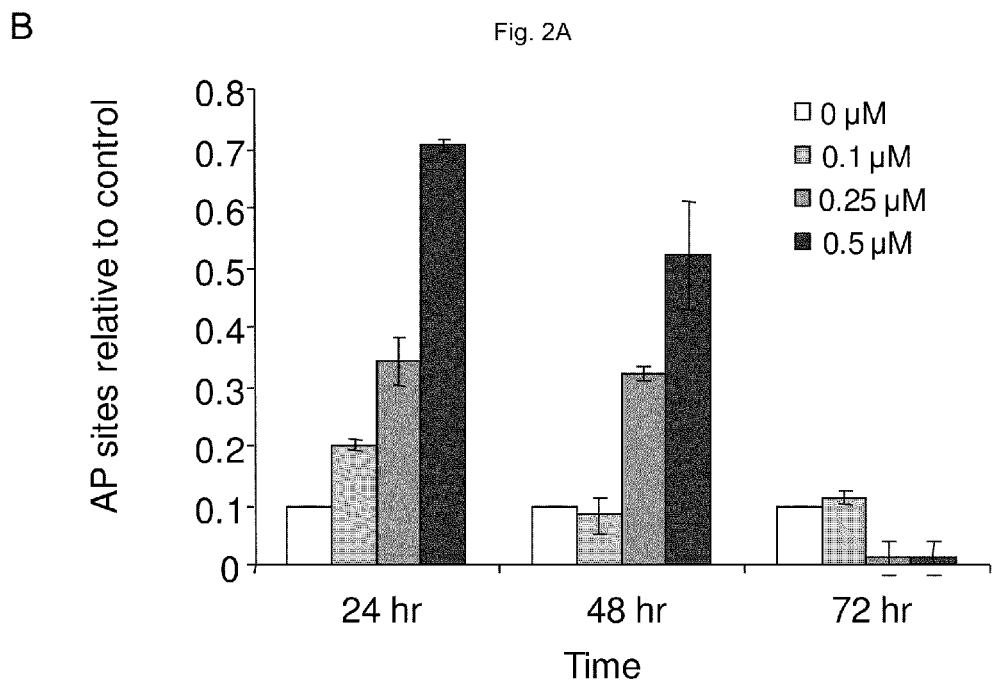
Figure 5:
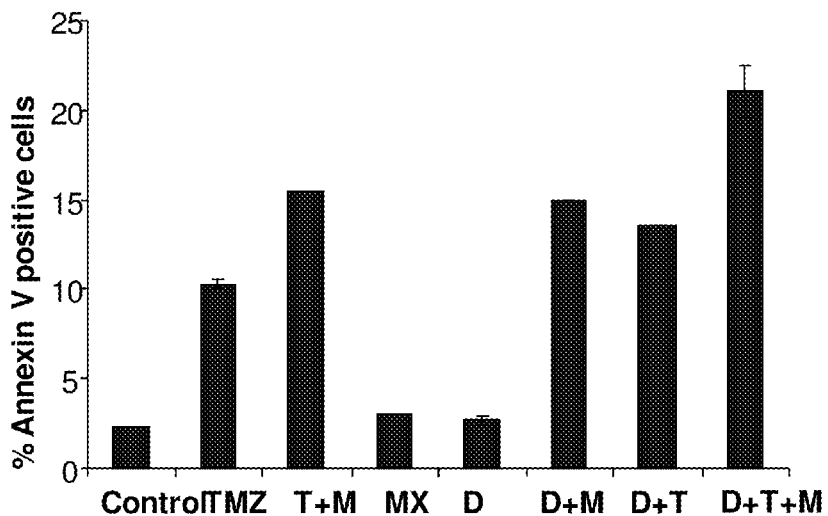
FIG. 5 illustrates a chart showing apoptotic death is increased by a combined treatment of decitabine and methoxyamine.
Figure 6:
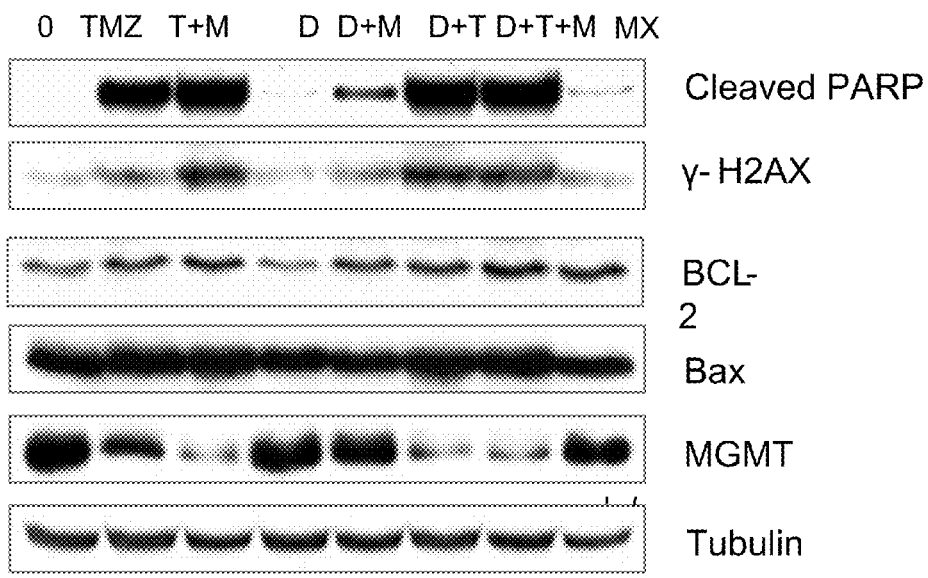
FIG. 6 illustrates an immunoblot showing cell death markers measured in the cells treated in FIG. 5.
Figure 7:
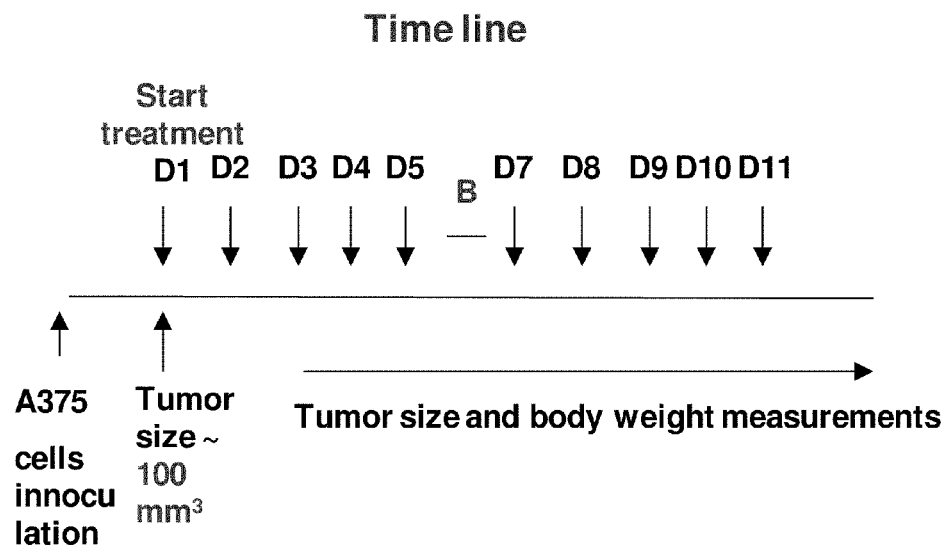
FIG. 7 illustrates a plot showing a time line of tumor treatment with methoxyamine and decitabine in human xenografts in mice.
Figure 8:
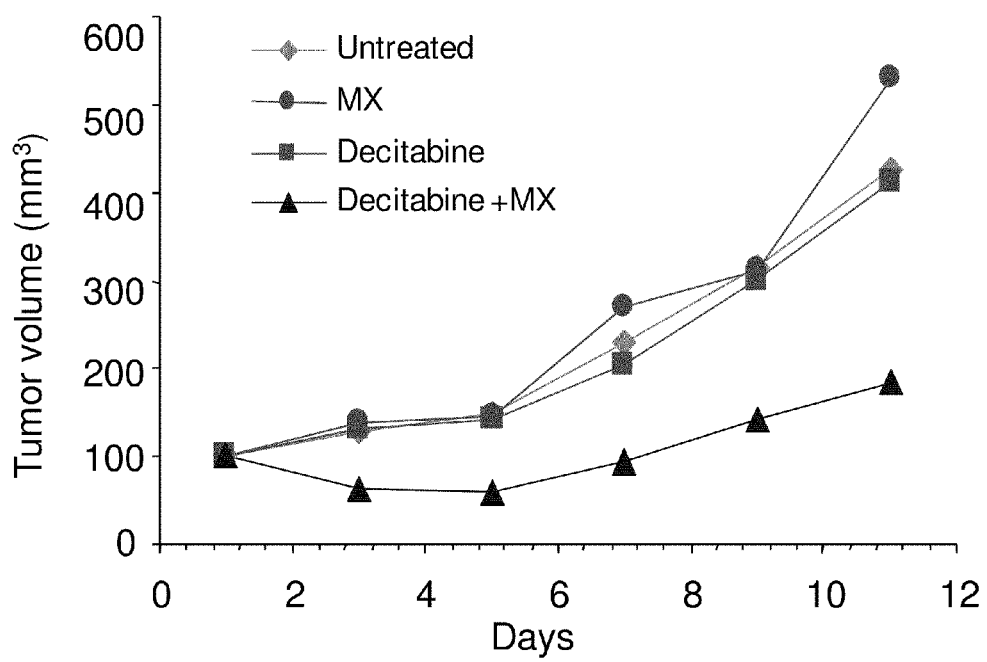
FIG. 8 illustrates a plot of tumor volume in human xenografts treated with methoxyamine and decitabine as illustrated in FIG. 7.
Figure 9:
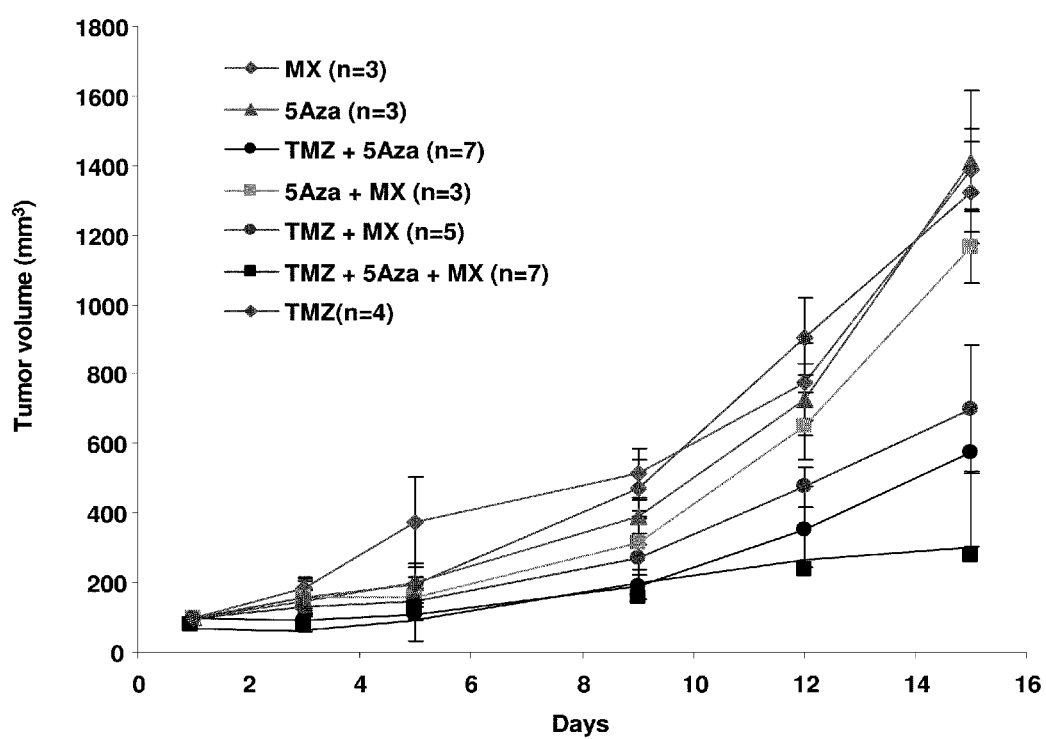
FIG. 9 illustrates plots showing combined treatment of A375 xenografts in mice treated with methoxyamine, decitabine, (5aza) and/or TMZ.

Decitabine-induced abasic sites (AP-sites) were increased proportionally with dose and duration of exposure (FIGS. 2 A-B). MX reduced the number of available AP-sites up to 80% indicating formation of stable MX-bound AP-sites that have the potential to interrupt BER pathway. A similar correlation between decitabine dose and the AP-sites formed was observed after in vitro exposure of primary AML cells to increase concentrations of decitabine. MX was able to bind a significant percentage (up to 60%) of these AP sites. Decitabine cytotoxicity was potentiated by MX. Cell survival assays demonstrated a 4-fold decrease in the $IC_{50}$ for decitabine when cells were co-treated with MX ($IC_{50\ dec}$=4 μM and $IC_{50\ Dec+MX}$=1 μM) (FIGS. 3-6). Apoptotic cell death measurements using Annexin V staining showed a 5-fold increase in cell death when cells following decitabine and MX. These events were accompanied by a concomitant increase in cleavage of PARP, and in γH2AX. Moreover, MX enhanced decitabine-induced antitumor effect in mice bearing A375 human melanoma xenografts, as measured by tumor growth delay: 7 days (0.5 mg/kg decitabine) versus 14 days (0.5 mg/kg decitabine plus 2 mg/kg MX) (FIGS. 7-9).

These studies not only suggests for the first time the role of BER in the processing of incorporated decitabine, but they also provide insights into a new and promising cancer therapeutic strategy of combining decutabine with MX to block BER.

Figure 3:
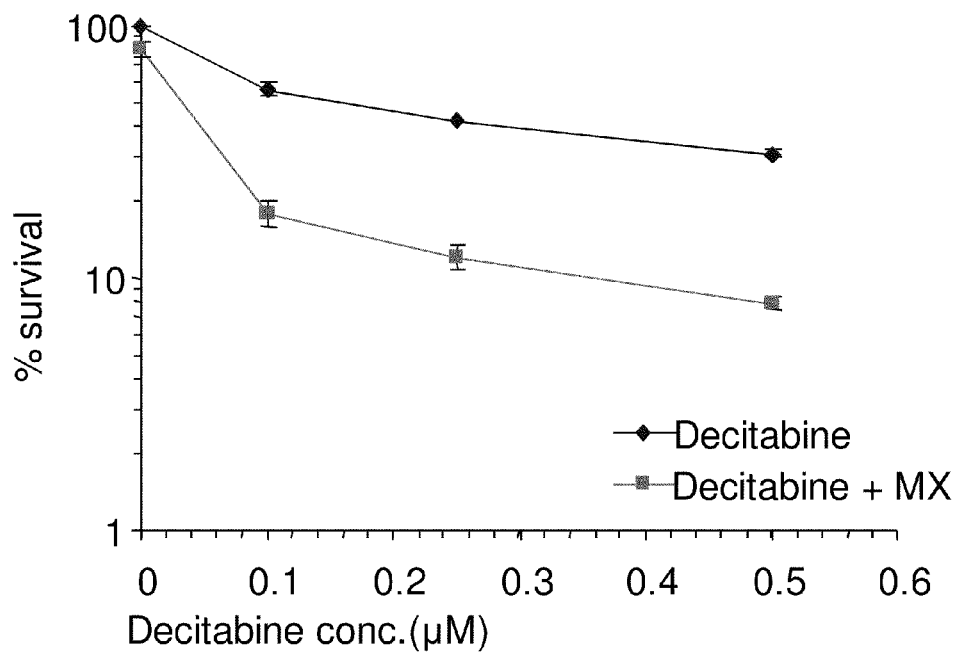
FIG. 3 illustrates a plot of a clonogenic survival assay in cells treated with decitabine and methoxyamine.
Figure 4:
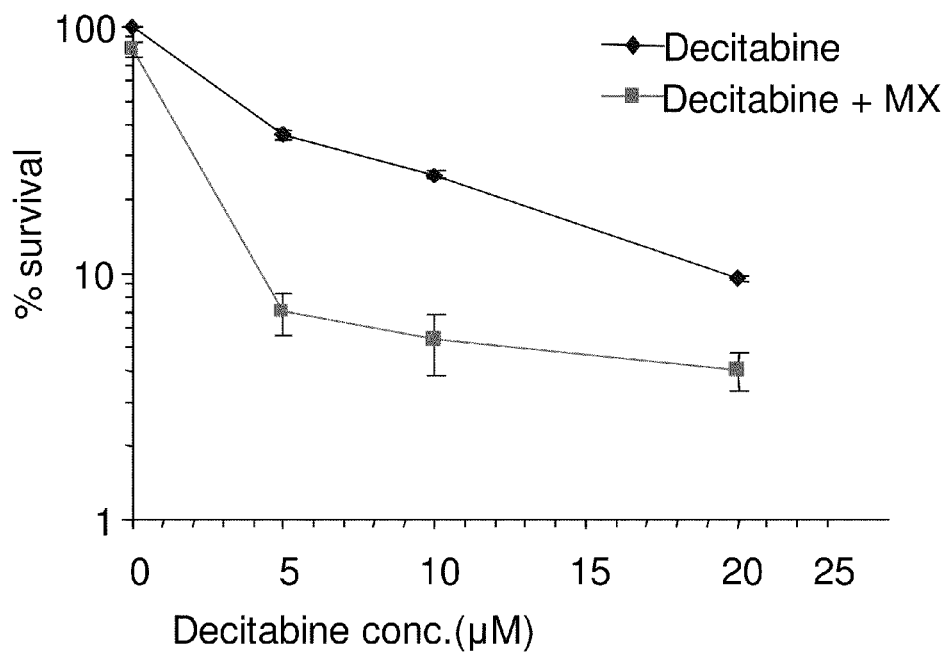
FIG. 4 illustrates a plot of clonogenic survival assay in cells treated with decitabine and methoxyamine.

Incorporation of Decitabine (5-aza-dC) into DNA Activates the BER Pathway and MX Potentiates 5-aza-dC Cytotoxicity Through Blocking BER in Melanoma Cells AP Sites Formed by 5-aza-dC in Cells To test whether the incorporation of 5-aza-dC activates the cellular BER pathway that removes 5-aza-dC as an abnormal base and generates an AP site, we examined the formation of AP sites in cellular DNA after cells were exposed to various concentrations of 5-aza-dC (0, 0.1-20 µM) for 24 h. The increase in formation of AP sites following treatment with 5-aza-dC was observed, as detected by ARP reagent. We also examined whether MX recognizes and binds to AP sites produced by 5-aza-dC; if so, co-treatment with MX would reduce detectable AP sites. We have introduced that ARP reagent competitively binds to AP sites with MX, and it detects only free AP sites, but not MX-bound AP sites. As shown in FIGS. 2 A-B, AP sites increase proportionally with increasing 5-aza-dC concentrations, from 0.1-5 µM. In contrast, relatively low levels of AP sites were detected at higher concentrations (10 and 20 µM) of 5-aza-dC; probably, a higher percentage of cells were dead or dying after exposure to high doses of the drug. The combination with MX reduced AP sites. The levels of MX-bound AP sites were determined based on the differences between the levels of AP sites in cells treated with 5-aza-dC alone and with the combination of 5-aza-dC and MX. The clonogenic survival assays (FIGS. 3-4) showed that MX enhanced 5-aza-dC killing effect by 5 folds. The IC90 value was 4 µM for TMZ combined with MX, compared to 20 µM for 5-aza-dC alone (FIGS. 3-4).

The Combination of 5-aza-dC and MX Treatment Synergistically Induced Apoptosis in A375 Melanoma Cells To examine the consequence of MX targeting the AP sites produced by 5-aza-dC, using flow cytometry of Annexin V-FITC, we analyzed and compared the percentage of apoptotic cells induced by treatment with the combination of 5-aza-dC and MX or drugs alone. When cells were treated with 5-aza-dC (5 µM for 2 h) or MX alone (12.5 mM for 2 h and 3 mM for 24 h), 97% of cells remained viable at 24 h after treatment. In contrast, when cells were incubated with the combination of 5-aza-dC and MX, 5-fold more cells were killed by forcing target cells to go into apoptosis ($P<0.01$). The MX-protentiated cytotoxicity of 5-aza-dC was consistent with the results obtained from the survival assays (FIGS. 3-4). Similarly, enhanced induction of apoptosis was also observed in cells treated with TMZ plus 5-aza-dC or in combination with MX (FIG. 5). Thus, the combined treatments as compared with single treatment result in more effective apoptotic response in cells. FIG. 6 shows the expression levels of protein markers of cell death in response to TMZ, MX, 5-aza-dC alone or in combination.

Caspase activation is the final common molecular event required for execution of apoptosis in most biological systems. PARP is a cellular substrate that is cleaved by active caspase-3 during apoptosis. Thus, the levels of cleaved PARP act as a nuclear apoptotic landmark. To examine caspase activation, cell lysates obtained 24 hr after treatment of A375 cells with either, 5-aza-dC, TMZ, or MX alone or the combinations were analyzed for PARP cleavage. The increase in PARP cleavage activity was seen in cells treated with the combinations, indicating that the treatment-induced apoptosis was dependent on caspase-3 protease activity. Western blot analysis also revealed an increase in γH2AX in cells treated with TMZ and TMZ in combination with either MX or 5-aza-dC or both. H2AX phosphorylation has been demonstrated to be an early chromosome modification that is followed by apoptotic DNA fragmentation and constitutes an important step in the course of mammalian apoptosis. Our results showed that increased γH2AX was concomitant with the induction of cleaved PARP. We consistently propose that increased apoptotic death observed in this study is related to the DNA DSBs induced by the blocking BER pathway. MGMT protein levels were measured in cells to confirm that as an alkylating agent, TMZ inhibits MGMT; 5-aza-dC as a demethylation agent does not affect the expression of MGMT. Results indicate that the re-expression of MGMT in melanoma cells by the combination of TMZ and 5-aza-dC is not the concern.

Antitumor Activity of TMZ with 5-aza-dC and MX In Vivo

Next, we tested the effect of TMZ with 5-aza-dC and MX on the progression of established A375 melanoma xenograft tumors in nude mice (FIG. 9). We treated mice bearing s.c. tumors (~100 mm$^3$) with vehicle control (PBS), TMZ (80 mg/kg), 5-aza-dC (0.75 mg/kg), and MX (2 mg/kg), and the combinations, ip injection, daily ×3 days for 2 consecutive cycles. Treatment with TMZ alone had a minor effect on the overall growth of A375 tumors compared to the vehicle control. In contrast, further tumor growth in the mice treated with the combination of TMZ with MX or 5-aza-dC was prevented, and efficient inhibition of tumor growth was seen in mice treated with the combination of all three drugs ($P<0.02$); at day 15, tumor volume was only ⅙ of that in control mice. However, the inhibition of tumor growth using the MX, 5-azadC combination was not optimal and needs to be pursued with additional dose and time course studies. As compared with control animals, no additive toxicity (based on the assessment of body weight) was observed in mice receiving combined treatment.

General Methods

Immunohistochemistry

Formalin-fixed and paraffin-embedded mice tissue sections are examined for BER proteins and active AKT, PTEN, and expression of Topo IIα using the 3,3'-diaminobenzidine kits (Ventana Medical Systems, Tucson, Ariz.). The slides are deparaffinized with xylin and graded alcohol and treated with citrate buffer (pH 6) for 20 min for antigen retrieval. The slides are incubated with primary antibodies (1:100 dilution) at 4° C. overnight, followed by secondary antibody at room temperature for 1 hr. Sections are counterstained with hematoxylin and examined under the microscope, with representative areas being photographed using a ×20 objective.

Immunofluorescence Microsopy

Cells are grown on coverslips and treated with MX plus TMZ or with each drug separately for 24, 48, and 72 hrs. Both treated and untreated cells are fixed in 2% paraformaldehyde and permeabilized with 0.2% Triton-100x. Cells are incubated with primary antibodies to proteins such as γH2AX (Upstate Biotechnology), topo II (Santa Cruz), or BER proteins and then followed by secondary antibodies conjugated to Alexa 488 (green) or Alexa 633 (red), respectively (Molecular Probes). Images are digitally captured using an Olympus microscope equipped with a digital camera.

Western Blotting

Cell or tissue lysates (50 µg in buffer containing 1% NP40, 20 mM HEPES, 4 mM EDTA, 1 mM phenylmethylsulfonyl fluoride, 50 µg/ml trypsin inhibitor, 5 mM benzamidine, and 1 µg/ml each of aprotinin, leupeptin, and pepstatin) are separated by SDS-PAGE and electrotransferred onto nitrocellulose membranes. Blots are blocked with 5% nonfat dry milk in 0.1% Tween 20 in PBS for 1 h at room temperature and incubated overnight at 4° C. with primary antibodies, according to the manufacturer's recommended dilution, followed by incubation with secondary horseradish peroxidase-conjugated antibodies (Amersham Biosciences) for 1 h at 37° C. β-Actin is used as an internal standard for protein loading. Immunoreactive bands are visualized by enhanced chemiluminescence and subsequent exposure to hyperfilm (X-ray film; Eastman Kodak).

Assessment of Apoptosis by Annexin V Staining

For annexin V-FITC staining, $1 \times 10^6$ cells are washed twice with cold PBS and then resuspended in 1× binding buffer (10 mM HEPES [N-2-hydroxyethylpiperazine-N'-2-ethanesulfonic acid]/NaOH, pH7.4, 140 mM NaOH, 2.5 mM $CaCl_2$). The cells are incubated with annexin V-FITC (BD PharMingen, San Diego, Calif.) and 5 μg/mL propidium iodide (PI), and incubated for 15 minutes at room temperature in the dark per the manufacturer's instructions. The samples are analyzed by flow cytometry within 1 hour to determine the percentage of cells displaying annexin V staining (early apoptosis) or both annexin V and PI staining (late apoptosis).

AP Site Assay

The AP sites are measured using ARP, which competitively reacts with MX to bind to an aldehyde group at AP sites. Thus, this reagent detects only MX-free AP sites. The assay is performed as previously described with minor modifications (24, 32-34). Briefly, cells ($2 \times 10^6$) are plated and exposed to TMZ or 5-aza-dC (with increasing concentrations) with or without MX. Cells are collected at 4 or 24 hr after treatment and dose-dependent AP sites are measured. Alternatively, for the time-dependent assay, cells are exposed to drug at IC50 values with or without MX for a period of 72 hrs. Cells are harvested at 24, 48, and 72 hr, respectively. After extracting by phenol (Fischer Scientific, Fair Lawn, N.J.) and chloroform (Sigma-Aldrich, St. Louis, Mo.), DNA (10 μg) is incubated with 15 μl of 1 mM ARP (Dojindo Laboratories, Kumamoto, Japan) in 150 μl PBS solution at 37° C. for 15 min. DNA is then precipitated with 400 μl ice-cold ethanol (100%) at −20° C. for 20 min and washed with 70% ethanol. DNA is dried at room temperature for 30 min and then resuspended in TE buffer to achieve a final concentration of 0.3 μg/100 μl. The ARP-labeled DNA is then heat-denatured at 100° C. for 5 min, quickly chilled on ice and mixed with an equal amount of 2 M ammonium acetate. The DNA is then immobilized on BA-S 85 nitrocellulose membrane (Schleicher and Schuell, Dassel, Germany) using a minifold II vacuum filter device (Schleicher and Schuell, Dassel, Germany). The membrane is baked at 80° C. for 1 hr and incubated with 0.25% BSA/PBS containing streptavidin-conjugated horseradish peroxidase (BioGenex, SanRamon, Calif.) at room temperature for 40 min with gentle shaking. ARP-labeled AP sites are visualized by chemiluminescence (Amersham Corp, Piscataway, N.J.) followed by quantitative densitometry using NIH ImageJ software.

The Alkaline and Neutral Single Cell Gel Electrophoresis (Comet) Assay

The Comet assay is based on the ability of denatured, cleaved DNA fragments to migrate out of fixed cells under the influence of an electric field. Undamaged DNA migrates slower and remains within the confines of the nuclei when a current is applied. The single cell Comet electrophoresis assay is performed using a Comet Assay kit (Trevigen, Gaithersburg, Md.). Approximately 5000 (in 50 μl) cells after the treatment are mixed with 250 μl of 1% low melting point agarose in 1×PBS at 37° C. The mixture (75 μl) is quickly pipetted onto a Comet slide (Trevigen, Gaithersburg, Md.) and allowed to solidify at 4° C. Slides are immersed for 30 min in prechilled lysis buffer (2.5 mM sodium chloride, 100 mM EDTA pH 10, 10 mM Tris Base, 1% sodium lauryl sarcosinate, 0.01% Triton X-100) at 4° C. After lyses, slides are incubated for 20 min in alkali solution (0.3 M NaOH, 1 mM EDTA) at room temperature to allow unwinding of DNA and then subjected to both neutral and alkaline electrophoresis for the next 20 min. Comet in an individual cell is stained with Comet silver staining kit (Trevigen, Gaithersburg, Md.) and visualized using an online CCD camera. Fifty cells per treatment are analyzed using NIH ImageJ software to generate quantitative and statistical data. Cellular DNA damage is expressed as the "tail moment" that combines a measurement of the length of the DNA migration and the relative DNA content therein.

Clonogenic Survival Assay

Cells (2000/dish) are plated and treated with TMZ or 5-aza-dC, with or without MX. After treatment, the drugs are removed, and fresh medium is added to the cells for 7 days. Surviving colonies are stained with methylene blue for 30 min at room temperature, and the colonies containing more than 50 cells are counted to generate survival curves. To assess drug-induced cytotoxicity, the ratio of the IC50 of the initial drug alone to that obtained for the combination is calculated. This ratio is referred to as the DMF parameter and indicates the degree of potentiation of cytotoxicity by the modulator.

Xenograft Studies

These studies will test the antitumor effect of TMZ alone and in combination with MX and decitabine on melanoma xenografts in athymic mice.

Tumor cells ($5 \times 10^6$) are injected into bilateral flanks of female athymic nude mice (6-8 weeks of age). When the volume of tumor nodules reached 100-150 $mm^3$, mice are randomly assigned to control or treatment groups (6-10 mice/group).

Tumor measurement: Tumors are measured with calipers using the formula: $V = L (mm) \times W^2 (mm)/2$, where L is the largest diameter and W is the smallest diameter of the tumor. Tumor measurements will be taken every 3 days. The relative tumor volume (V/V0) is calculated by dividing the measured tumor volume (V) by the initial tumor volume (V0) at day 0.

End point: Tumor responses are quantified by tumor regrowth delay, where tumor growth delay=T2x−C2x; T2x and C2x represent the number of days that treated (T) and control (C) tumors take to double in size from the day of treatment, respectively.

Those skilled in the art will recognize, or be able to ascertain using no more than routine experimentation, numerous equivalents to the compounds and methods of use thereof described herein. Such equivalents are considered to be within the scope of this invention and are covered by the following claims. All patents, publications, and references cited in the present application are herein incorporated by reference in their entirety.

Having described the invention, the following is claimed:

1. A method of treating cancer in a subject comprising:
    administering to the subject a therapeutically effective amount of 5-aza-2'-deoxycytidine that induces formation of AP sites in cancer cells of the subjects and an amount AP endonuclease inhibitor effective to potentiate the cytotoxicity of the 5-aza-2'-deoxycytidine to the cancer cells, the AP endonuclease inhibitor being a small molecule with a primary amine group that forms a covalent linkage with an aldehyde group of an AP site induced by 5-aza-2'-deoxycytidine, wherein the amount of the AP endonuclease inhibitor is an amount sufficient to sensitize the cancer cells without causing undue sensitization of normal cells.

2. The method of claim 1, the AP endonuclease inhibitor is selected from group consisting of methoxyamine, O-benzylhydroxylamine; ethyl aminooxyacetate; aminooxyacetic acid; ethyl aminooxyacetate; H₂NOCHMeCO₂H; carboxymethoxyamine; aminooxyacetic acid; HN=C(NH₂)SCH₂CH₂ONH₂; H₂NO(CH₂)₃SC(NH₂)=NH; MeOC(O)CH(NH₂)CH₂ONH₂; H₂NOCH₂CH(NH₂)CO₂H; canaline; H₂NO(CH₂)₄ONH₂; O-(p-nitrobenzyl)hydroxylamine; 2-amino-4-(aminooxymethyl)thiazole; 4-(aminooxymethyl)thiazole; O,O'-(o-phenylenedimethylene)dihydroxylamine; 2,4-dinitrophenoxyamine; O,O'-(m-phenylenedimethylene)dihydroxylamine; O,O'-(p-phenylenedimethylene)dihydroxylamine; H₂C=CHCH₂ONH₂; H₂NO(CH₂)₄ONH₂; H₃C—(CH₂)₁₅—O—NH₂, 2,2'-(1,2-ethanediyl)bis(3-aminooxy)butenedioic acid dimethyl diethyl ester;

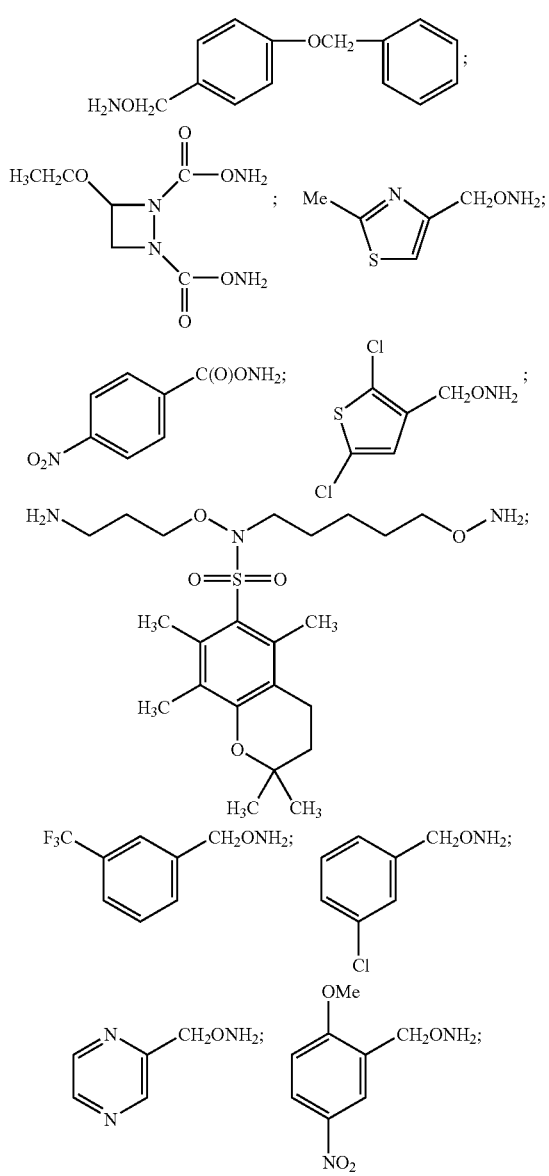

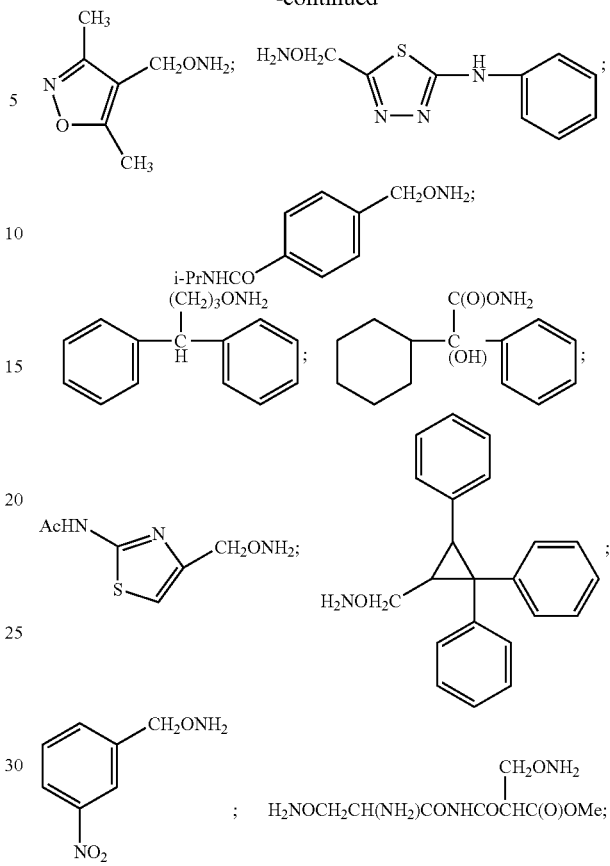

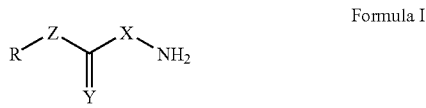

a compound having a structure of Formula I:

$$R^{-Z}\underset{Y}{\overset{X}{\downarrow}}NH_2 \quad \text{Formula I}$$

wherein X is O or NH,
Y is O, S, or NH,
Z is absent or represents O, S, or NH, and
R represents a hydrogen or a hydrocarbon moiety,
and pharmaceutically acceptable salts thereof.

3. The method of claim 1, the AP endonuclease inhibitor comprising methoxyamine.

4. The method of claim 1, further comprising administering an anticancer agent to the subject.

5. The method of claim 4, the anticancer agent comprising an alkylating agent.

6. The method of claim 1, wherein the amount of 5-aza-2'-deoxycytidine is subtherapeutic when administered in the absence of the AP endonuclease inhibitor.

7. The method of claim 1, wherein the subject is selected as having a cancer at least partially resistant to treatment with 5-aza-2'-deoxycytidine alone, and wherein the AP endonuclease inhibitor is administered in an amount effective to potentiate the activity of the 5-aza-2'-deoxycytidine and overcome the resistance.

8. The method of claim 1, wherein said cancer is selected from the group consisting of carcinomas, melanomas, sarcomas, lymphomas, leukemias, astrocytomas, gliomas, malignant melanomas, chronic lymphocytic leukemia, lung cancers, colorectal cancers, ovarian cancers, pancreatic cancers, renal cancers, endometrial cancers, gastric cancers, liver cancers, head and neck cancers, and breast cancers.

9. A method of treating cancer in a subject comprising: administering to the subject a therapeutically effective amount of 5-aza-2'-deoxycytidine that induces formation of AP sites in cancer cells of the subjects and an amount of methoxyamine effective to potentiate the cytotoxicity of the 5-aza-2'-deoxycytidine to the cancer cells, wherein the amount of the methoxyamine is an amount sufficient to sensitize the cancer cells without causing undue sensitization of normal cells.

10. The method of claim 9, further comprising administering an alkylating agent to the subject.

11. The method of claim 9, wherein the amount of 5-aza-2'-deoxycytidine is subtherapeutic when administered in the absence of the methoxyamine.

12. The method of claim 9, wherein the subject is selected as having a cancer at least partially resistant to treatment with 5-aza-2'-deoxycytidine alone, and wherein the methoxyamine is administered in an amount effective to potentiate the activity of the 5-aza-2'-deoxycytidine and overcome the resistance.

13. The method of claim 9, wherein said cancer is selected from the group consisting of carcinomas, melanomas, sarcomas, lymphomas, leukemias, astrocytomas, gliomas, malignant melanomas, chronic lymphocytic leukemia, lung cancers, colorectal cancers, ovarian cancers, pancreatic cancers, renal cancers, endometrial cancers, gastric cancers, liver cancers, head and neck cancers, and breast cancers.

14. A method of treating cancer in a subject comprising: administering to the subject a therapeutically effective amount of 5-aza-2'-deoxycytidine and methoxyamine, the methoxyamine being administered at an amount effective to potentiate the cytotoxicity of the 5-aza-2'-deoxycytidine to the cancer cells, wherein the amount of the methoxyamine is an amount sufficient to sensitize the cancer cells without causing undue sensitization of normal cells.

15. The method of claim 14, further comprising administering an alkylating agent to the subject.

16. The method of claim 14, wherein the subject is selected as having a cancer at least partially resistant to treatment with 5-aza-2'-deoxycytidine alone, and wherein the methoxyamine is administered in an amount effective to potentiate the activity of the antimetabolite agent and overcome the resistance.

17. The method of claim 14, wherein said cancer is selected from the group consisting of carcinomas, melanomas, sarcomas, lymphomas, leukemias, astrocytomas, gliomas, malignant melanomas, chronic lymphocytic leukemia, lung cancers, colorectal cancers, ovarian cancers, pancreatic cancers, renal cancers, endometrial cancers, gastric cancers, liver cancers, head and neck cancers, and breast cancers.

18. The method of claim 14, wherein the cancer is a melanoma.

* * * * *